(12) United States Patent
Olsen et al.

(10) Patent No.: US 6,814,720 B2
(45) Date of Patent: Nov. 9, 2004

(54) COLLECTING BAG

(75) Inventors: Eskil Hoelland Olsen, Humlebaek (DK); Henrik Leisner, Gentofte (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/169,065

(22) PCT Filed: Jan. 26, 2001

(86) PCT No.: PCT/DK01/00062

§ 371 (c)(1),
(2), (4) Date: Jul. 3, 2002

(87) PCT Pub. No.: WO01/54632

PCT Pub. Date: Aug. 2, 2001

(65) Prior Publication Data

US 2003/0060786 A1 Mar. 27, 2003

(30) Foreign Application Priority Data

Jan. 28, 2000 (DK) .......................................... 2000 00154
Oct. 30, 2000 (DK) .......................................... 2000 01624

(51) Int. Cl.[7] .................................................. A61F 5/44
(52) U.S. Cl. ...................................... 604/339; 337/344
(58) Field of Search ................................ 604/332–344, 604/345, 355

(56) References Cited

U.S. PATENT DOCUMENTS

| | | | |
|---|---|---|---|
| 3,604,421 A | 9/1971 | Pizzella | 128/283 |
| 4,095,599 A | 6/1978 | Simonet-Haibe | 128/283 |
| 4,367,732 A | 1/1983 | Poulsen et al. | 128/156 |

FOREIGN PATENT DOCUMENTS

| | | | | |
|---|---|---|---|---|
| EP | 0 276 042 | 7/1988 | | |
| GB | 2 017 501 | 10/1979 | | |
| WO | WO 96/38106 | * 12/1996 | ........... | A61F/5/448 |
| WO | 00/30576 | 6/2000 | | |

* cited by examiner

*Primary Examiner*—John J. Calvert
*Assistant Examiner*—Linh Truong
(74) *Attorney, Agent, or Firm*—Jacobson Holman PLLC

(57) ABSTRACT

A flange for a medical collecting bag having an aperture allowing bodily fluids or exudates to enter the bag. The flange has an inner rim delimiting the aperture therein, and a central area encircling the aperture, which area has a predetermined weakening line pattern. The force needed for removing the bag flange from the skin or a body side member is smaller than the force needed for breaking the weakening lines which enables a simple gradual enlargement of the aperture of an ostomy device for adaptation of the aperture to the size of the stoma or for adaptation of the aperture to the size of a wound, as well as a complete removal of the bag flange when substituting the bag.

17 Claims, 7 Drawing Sheets

Fig. 2
Fig. 3
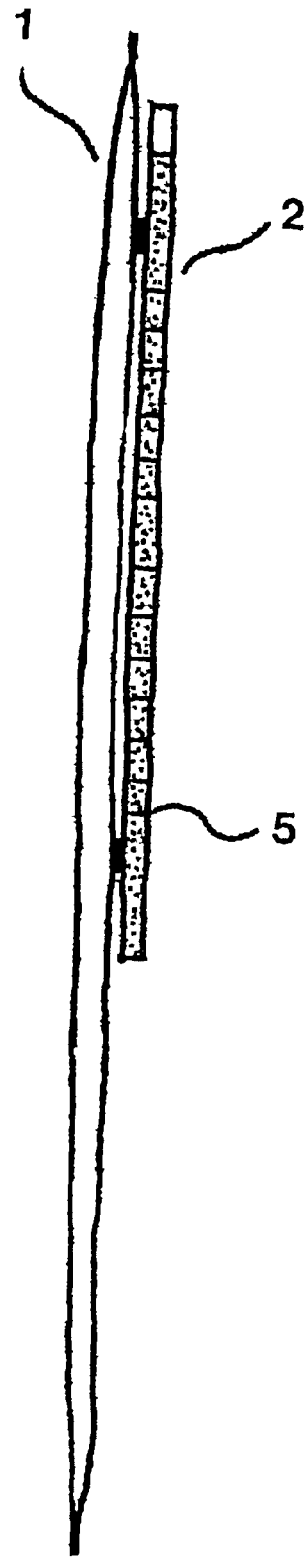
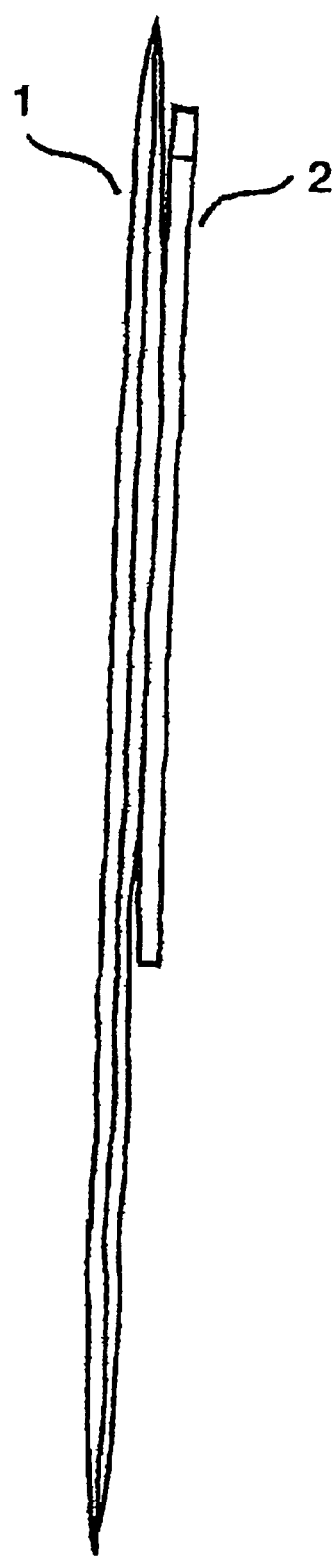

COLLECTING BAG

This is a nationalization of PCT/DK01/00062 filed Jan. 26, 2001 and published in English.

FIELD OF THE INVENTION

The present invention relates to a medical appliance comprising a body side member comprising an adhesive wafer for securing the appliance to the patient's skin, said wafer or pad having an aperture allowing bodily fluids or exudates to enter the appliance, and an optionally separately exchangeable collecting bag secured to the body side ostomy member for collecting fluids or excretions.

BACKGROUND OF THE INVENTION

In connection with surgery for a number of diseases in the gastrointestinal tract a consequence is, in many cases, that the colon, the ileum or the urethra is exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula which has developed between an internal organ and the abdominal surface, the patient will have to rely on an appliance to collect the bodily material emerging from such opening. Collecting bags may also be used for collecting exudates from a wound or collection of bodily material in connection with post operation or drainage purposes.

Such appliances are well known and may be two-piece or one-piece appliances. In both types of appliances, a body side member is attached to the wearer's abdomen, and optionally a collecting member or bag is attached to the body side member for collecting exudates from the stoma or wound in case of a two-piece appliance.

When using one-piece appliances, the whole appliance, including the adhesive wafer or pad securing the appliance to the skin is removed and replaced by a fresh appliance. When using two-piece appliances, the body side member is left in place for several days, and only the collecting member or bag is replaced.

The service time of the body side ostomy member depends on the amount and aggressiveness of the exudates and of the tightness between the ostomy and the body side ostomy member.

DESCRIPTION OF THE RELATED ART

The service time of ostomy appliances may be reduced for several reasons. Due to the aggressiveness of the exudates, the adhesive material of the adhesive wafer may deteriorate and give access to the skin for the exudates. This may call for a change of appliance in order to protect the skin. Furthermore, a leakage around the stoma may give rise to appearance of unpleasant materials or odours at the abdomen of the patient which may give rise to skin problems as well as embarrassing situations. In order to increase the service time of especially ostomy appliances it has been proposed to adapt the size of the aperture of the adhesive wafer to the size of the actual stoma. One-piece ostomy appliances and body side members of two-piece ostomy appliances are normally offered having adhesive wafers having a range of sizes of apertures for better adaptation to the size of the actual stoma and the adhesive wafer is often provided with a cutting guide typically having series of concentric printed lines having an indication of the diameter thereof for facilitating a more accurate customisation using e.g. scissors.

GB Patent Application No. 2 017 501 discloses a device for sealing an ostomy bag to the skin of a patient which device comprises a sheet of material capable of adhering to the skin of a patient and having a slit or cut extending as a spiral or the like. An aperture may then be produced in the sheet by unwinding the coil defined by the slit. The sheet may be of a gelatinous material having a basis of Karaya gum and/or another hydrophilic material.

The appliances disclosed in GB Patent Application No. 2 017 501 are one-piece appliances.

U.S. Pat. No. 3,604,421 discloses a one piece disposable bag having a variable size opening surrounded by separately removable concentric annular strips for forming an opening of variable diameter. However U.S. Pat. No. 3,604,421 is silent with respect to the problems associated with removal of all of the bag when substituting the bag.

These two references are silent with respect to problems concerning a complete removal of the bag flange of the appliances when substituting the bag and both teach the presence of a central disc to be removed before using the appliance.

In connection with two-piece appliances, the size of the aperture of the collecting bag for receiving a stoma is often greater than the size of the apertures of the commonly used body side members, and there is a considerable risk of access of exudates to the distal surface of the adhesive wafer of the body side member. This opens the door for chemical attack on the adhesive from the "back" and may furthermore give rise to soiling or contamination of the distal surface of the body side member, especially in connection with ileo-stomies and colostomies. This may reduce the wearing time of the body side member and furthermore give rise to problems when substituting the collecting bag with a fresh bag as the coupling area may have to be cleaned in order to ensure a proper coupling and sealing of the fresh bag and also to ensure that residues giving rise to unpleasant odours are not left on the body side member. Altogether there is a considerable risk of having to exchange the body side member before its technical service time has been exhausted.

It has been found that these drawbacks may be alleviated by the present invention.

SUMMARY OF THE INVENTION

The invention relates in its broadest aspect to a medical appliance comprising a body side member comprising a flange in the form of an adhesive wafer for securing the appliance to a patient's skin, said wafer having an aperture allowing bodily fluids or exudates to enter the appliance, and an optionally separately exchangeable collecting bag secured to the body side member for collecting fluids or excretions, wherein the flange has an inner rim defining the aperture therein and a central area encircling the aperture which area has a predetermined weakening pattern.

The invention further relates to a medical appliance comprising a body side member comprising an adhesive wafer for securing the appliance to a patient's skin, said wafer having an aperture allowing bodily fluids or exudates to enter the appliance, and a separately exchangeable collecting bag having a bag flange having an aperture allowing bodily fluids or exudates to enter the appliance, wherein the body side member comprises first coupling means being fixedly connected to the body side member and the collecting bag comprises corresponding second coupling means adapted for releasable coupling and sealing to the body side member, wherein the bag flange has an inner rim defining the aperture therein and a central area encircling the aperture which area has a predetermined weakening pattern.

Furthermore, the invention relates to an ostomy collecting bag having a bag flange having an aperture allowing bodily fluids or exudates to enter the appliance, the bag comprising coupling means for releasable coupling and sealing to corresponding coupling means fixedly connected to a body side member comprising an adhesive wafer for securing the body side member to a patient's skin, said wafer having an aperture allowing bodily fluids or exudates to enter the appliance, wherein the bag flange has an inner rim defining the aperture therein and a central area encircling the aperture which area has a predetermined weakening pattern.

Still further, the invention relates to a flange for a medical collecting bag in the form of a substantially annular flange having an inner rim defining an aperture therein and a central area encircling the aperture which area has a predetermined weakening pattern

BRIEF DESCRIPTION OF THE DRAWINGS

The invention is described more in detail with reference to the drawings in which FIG. 2 shows a section of the embodiment shown in FIG. 1 along the line A—A, FIG. 3 shows the embodiment shown in FIG. 1 seen from the side.

DETAILED DESCRIPTION OF THE PRESENT INVENTION

Figure 1:
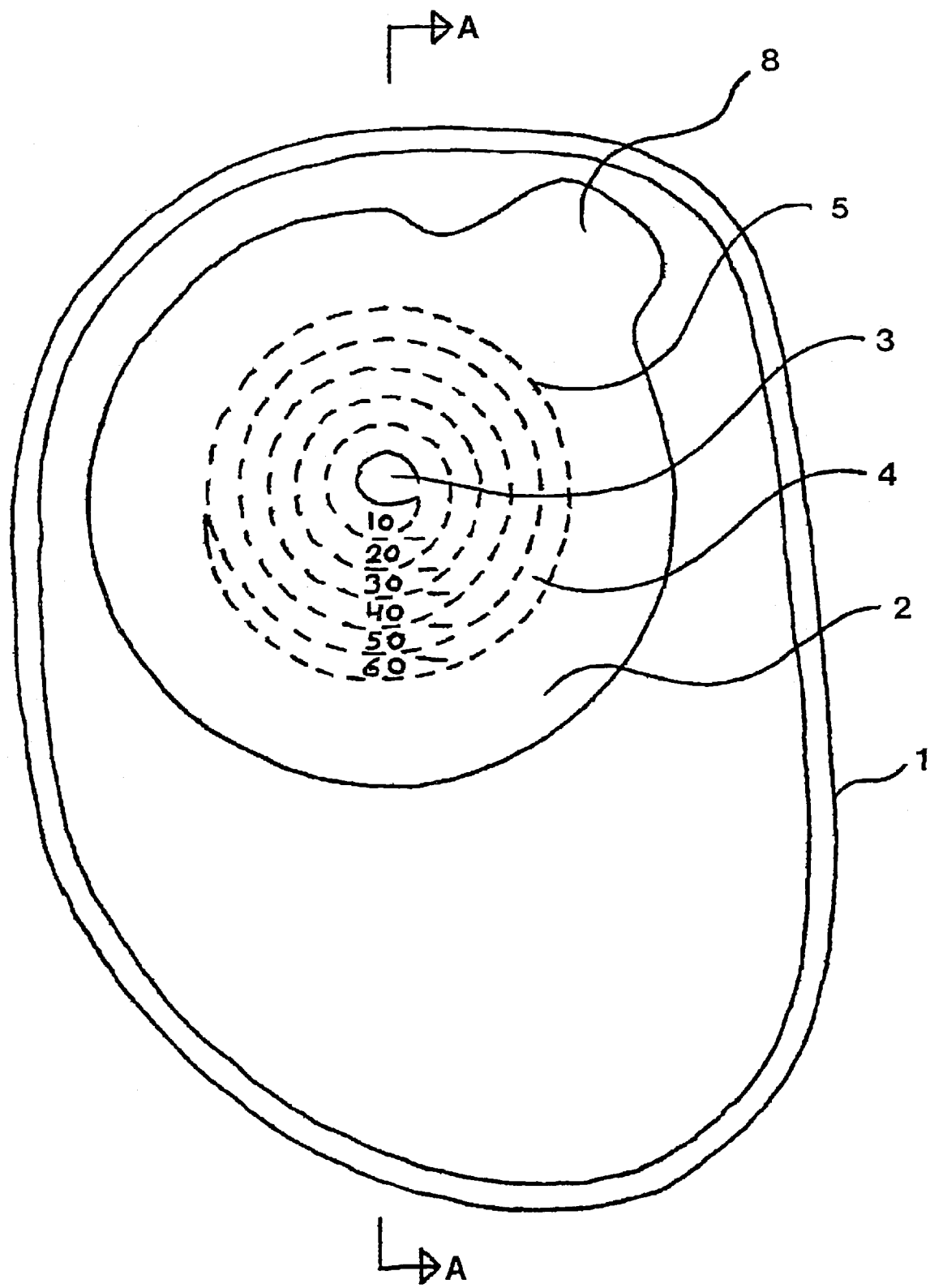
FIG. 1 shows an embodiment of a collecting bag according to the invention having a flange having a predetermined weakening line in the form of a helix.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention relates to a medical appliance comprising a body side member comprising a flange in the form of an adhesive wafer for securing the appliance to a patient's skin, said wafer having an aperture allowing bodily fluids or exudates to enter the appliance, and an optionally separately exchangeable collecting bag secured to the body side member for collecting fluids or excretions, wherein the flange has an inner rim defining the aperture therein and a central area encircling the aperture which area has a predetermined weakening pattern wherein the force needed for removing the bag flange from skin is smaller than the force needed for breaking the weakening lines.

Such an appliance of the invention including a collecting bag as an integral unit (not exchangeable) may be used as a one-piece ostomy appliance or for wound, post operation or drainage purposes offering a simple and effective alleviation of the above-mentioned drawbacks.

Furthermore, the present invention relates to a medical appliance comprising a body side member comprising an adhesive wafer for securing the appliance to a patient's skin, said wafer having an aperture allowing bodily fluids or exudates to enter the appliance, and a separately exchangeable collecting bag having a bag flange having an aperture allowing bodily fluids or exudates to enter the appliance, wherein the body side member comprises first coupling means being fixedly connected to the body side member and the collecting bag comprises corresponding second coupling means adapted for releasable coupling and sealing to the body side member, wherein the bag flange has an inner rim defining the aperture therein and a central area encircling the aperture which area has a predetermined weakening line pattern wherein the force needed for removing the bag flange from the body side member is smaller than the force needed for breaking the weakening lines.

The predetermined weakening line pattern renders it possible to adapt the aperture of a flange of an ostomy collection bag to the size of the actual stoma leading to a better protection of the skin or the distal surface of the adhesive wafer of the body side member reducing the contact with the aggressive exudates from a stoma and thus overcoming the above mentioned drawbacks. Furthermore, it is simple to adapt the aperture of the flange by a gradual enlargement for adaptation to the size of the stoma by tearing off a part of the flange along the inner rim using the fingers without having to rely on the use of tools.

Usually medical appliances such as ostomy appliances having an adhesive wafer for securing the appliance to a patient's skin are provided with skin-friendly adhesive which is preferably covered by a protecting cover or release liner which may for instance be siliconized paper. It does not need to have the same contour as the dressing, e.g. a number of dressings may be attached to a larger sheet of protective cover. The protective cover is not present during the use of the dressing of the invention. However, in accordance with a preferred embodiment of the invention a protecting cover is present for protecting the adhesive surface before use and during adaptation of the appliance to the individual ostomate.

The skin-friendly adhesive may be any skin-friendly adhesive known per se, e.g. an adhesive comprising hydrocolloids or other moisture absorbing constituents for prolonging the time of use. The adhesive may, for example, be of the type disclosed in U.S. Pat. No. 4,367,732.

It is preferred according to the invention that there is a difference in the breaking strength of the flange and that of the protective cover and that such difference is controlled so as to ensure that the breaking strength of the protective cover is lower than the breaking strength of the flange in order to enable an adaptation of the size of the aperture without removing the release liner. Thus, any unintended contact reducing the binding strength of the adhesive is avoided as is contamination with bacteria. Such difference in breaking strength is preferably obtained by controlling the pattern of weakening lines, leaving more minor "bridging" areas in the paper than in the flange when producing the weakening lines.

The aperture of the flange of a bag of the invention may thus be adapted to the actual shape of the stoma. This provides for a combination of the desired cleaning effect, comparable with the cleaning obtained from the "scraping" against the outer surface of the stoma by the inner rim of the adhesive wafer when exchanging a traditional one-piece ostomy appliance, with the advantage of leaving the body side member of a two-piece appliance on the abdomen of the ostomate for a longer span of time.

When the bag is attached to the body side member, the flange thereof furthermore protects the distal surface of the body side member and increases the service time and also reduces the soiling thereof.

The pattern of weakening lines may be any convenient pattern of e.g. in the form of punched or cut dots, slots or interrupted rectilinear or curved lines weakening the annular flange in a manner enabling removal of parts thereof from the inner rim of the flange. The pattern may be produced using any suitable process known per se for producing such penetrations of a sheet material such as cutting or punching.

The depth of cuts depends of the nature of the material and may penetrate only partially through the thickness of the flange although it is preferred that it penetrates completely through the flange at the rim of the aperture. It is preferred that weakening line penetrates completely through the thickness of the flange only leaving minor "bridging" areas being easily breakable for enlarging the aperture.

In one embodiment of the invention, the weakening pattern is in the form of an interrupted line pattern.

In a preferred embodiment of the invention, the weakening pattern is in the form of an interrupted helical line starting at the inner rim of the flange.

In another preferred embodiment of the invention, the weakening line pattern is in the form of a number of interrupted concentric lines surrounding the aperture in the second flange.

In a preferred embodiment of the invention, the weakening line pattern is in the form of a combination of helical or concentric lines and radial lines rendering it easy to adapt to the size and contour of the aperture to the stoma.

It is preferred to provide the outer part of the flange, outside the weakening pattern with perforations in an essentially circular zone corresponding of the kind disclosed in WO 00/30576 for further reducing the risk of leakage due to formation of canals.

The central area of the flange having an area having a predetermined weakening line pattern may according to another embodiment of the invention show only a weak adhesiveness. Thus, it is preferred that the adhesiveness of the central area is so weak that the force for removing the flange from the skin or the body side member is smaller that the force needed for breaking the weakening lines. This renders it possible to ensure a good contact to the skin or the back of the body side member being desirable for protecting the same against soiling and also ensures that the bag may be substituted without breaking the remaining weakening lines which may give rise to spilling of waste material situated on the flange inside the bag. In one embodiment of the invention it is ensured that the central area shows very low adhesiveness by utilising a flange having an adhesive having very low tack/peel values and it is also considered an embodiment of the invention to provide a flange not having adhesive in the central area. For practical reasons it is often less complicated to apply a layer of adhesive on all of the surface of the flange and then, afterwards to partially or fully disable the adhesive properties in the central area by applying an optionally perforated non-detachable cover layer covering the central area or e.g. by covering the adhesive layer of the central area partly or fully with a release agent such as talc. The cuts, dots, slots or interrupted rectilinear or curved lines preferably penetrates a cover layer.

In an especially preferred embodiment of the invention, the weakening pattern of the flange is in the form of concentric lines wherein the weakening pattern has at least one interruption in a radial zone from the aperture for receiving the stoma. Along this zone, the tearing resistance is higher than the force necessary for breaking the bridges connecting consecutive rings of the flange. This feature allows for a safe removal of an ostomy collecting bag together with all of the adhesive flange without leaving one or more rings on the body side member. The radial direction of such relative enforcement is preferably in the direction of a protruding part or ear facilitating the removal of the bag. In this embodiment, it is not necessary to rely on a weaker adhesiveness in the weakening line area in order to ensure a full removal of the bag and its flange as discussed above.

In another aspect, the invention relates to a medical collecting bag having a bag flange having an aperture allowing bodily fluids or exudates to enter the appliance, the bag comprising coupling means for releasable coupling and sealing to corresponding coupling means fixedly connected to a body side member comprising an adhesive wafer for securing the body side member to a patient's skin, said wafer having an aperture allowing bodily fluids or exudates to enter the bag, wherein the bag flange has an inner rim delimiting the aperture therein, and wherein the flange has a central area having a predetermined weakening line pattern wherein the force needed for removing the bag flange from the body side member is smaller than the force needed for breaking the weakening lines.

The coupling means may be any suitable coupling means known per se for coupling of ostomy body side members to ostomy collecting bags, e.g. a mechanical coupling such as matching coupling rings or it may be in the form of a first flange secured to the body side member and a second flange secured to the collecting bag, the second flange being adapted for removable and adhesive coupling and sealing to the first flange. Such second flange is suitably the above mentioned bag flange which then has outer adhesive areas for coupling to the body side member in addition to the central area.

The first and the second flanges are preferably formed as discs of a cellular plastic material, which provides a good shock absorbing and resilient action and also has the effect that the weight of the collecting system can be kept down.

In a third aspect, the invention relates to a flange for an ostomy collecting bag having a flange having an aperture allowing bodily fluids or exudates to enter the appliance, wherein the flange has an inner rim delimiting the aperture therein, and wherein the flange has a central area having a predetermined weakening line pattern wherein the force needed for removing the bag flange from the body side member is smaller than the force needed for breaking the weakening lines.

In the present context, the term "distal" in connection with a surface of an appliance is used to designate the surface thereof being opposite to the skin contacting surface thereof.

The term "medical" in connection with a bag or use is used to designate use in connection with collection of bodily fluids or excretions from a surface area or an aperture emerging on the surface of a living being. An appliance according to the invention may thus be a bag for placing on the skin for collecting wound exudates, bodily material in connection with post operation or drainage purposes or excretions from the urethra or the intestine which have led to an artificial opening in connection with an injury or surgery. A preferred use is for ostomy appliances or wound care appliances, mostly preferred being ostomy appliances.

DESCRIPTION OF THE PREFERRED EMBODIMENTS

Reference is made to FIG. 1 of the drawings showing an embodiment of an ostomy appliance according to the invention. The bag 1 comprises a flange 2 secured to the collecting bag which flange has an inner rim defining an inlet aperture 3 therein for receiving a stoma, and wherein the flange has a central area 4 having a predetermined weakening line pattern 5 in the form of a helical line starting from the inner rim thereof. The collecting bag 1 for collection of materials emerging from the stoma is adapted for coupling to a body side member for securing the bag 1 around the stoma on a patient's abdominal wall. The bag 1 may either be closed as shown or be openable at the bottom for intermittent emptying of its contents. The central area of the flange 2 is in this embodiment surrounded by a substantially annular part of the flange acting as coupling means for connecting the bag 1 sealingly with a body side member (not shown). Such a body side member comprises a body side member which is designed to be adhered to the patient's skin by means of a skin-friendly adhesive applied on the back of the body side member. The body side member carries first coupling means which in connection with this embodiment is in the form of a first flange or body side member flange, in which is formed an aperture and which is designed for receiving an adhesive coupling to the flange 2.

The body side member flange may be secured to the body side member with a layer of adhesive applied in a substantially annular connecting section having an internal diameter corresponding to that of the aperture in the body side member flange and having an external diameter so that a rim portion of the flange protrudes beyond the layer of an adhesive. Of course, the flange may also be secured to the body side member through other means, for example by welding.

The bag flange and a body side member flange may, for example, be moulded in a water-repellent cellular plastics material, such as ethylene vinyl acetate (EVA) or polyurethane (PUR), with closed cells so that the cellular plastic material does not absorb liquid.

The bag itself may made from any material known per se for the production of ostomy appliances.

On the side facing away from the bag, the flange is coated over substantially all its surface with a thin, washable layer of adhesive (not shown), which may, for example, be a hydrogel adhesive, an acrylate adhesive or an adhesive of the hot-melt type. The layer of adhesive is applied in a thin layer, partly to keep thickness low, and partly to maintain the flexibility and resilience of the bag flange. This application may be effected, for example, by coating, spraying or application in a suitable pattern. When the bag is delivered, the layer of adhesive is covered by a release liner.

The bag flange 2 preferably has a protruding part or ear 8 facilitating the removal of the bag by providing a handle or grip for handling the bag. In such an area, the adhesive is preferably covered by a cover layer.

FIG. 2 shows a sectional view of the embodiment of a bag of the invention shown in FIG. 2, taken along the line A—A before preparing the bag for application and indicating the cuts 5.

Figure 4:
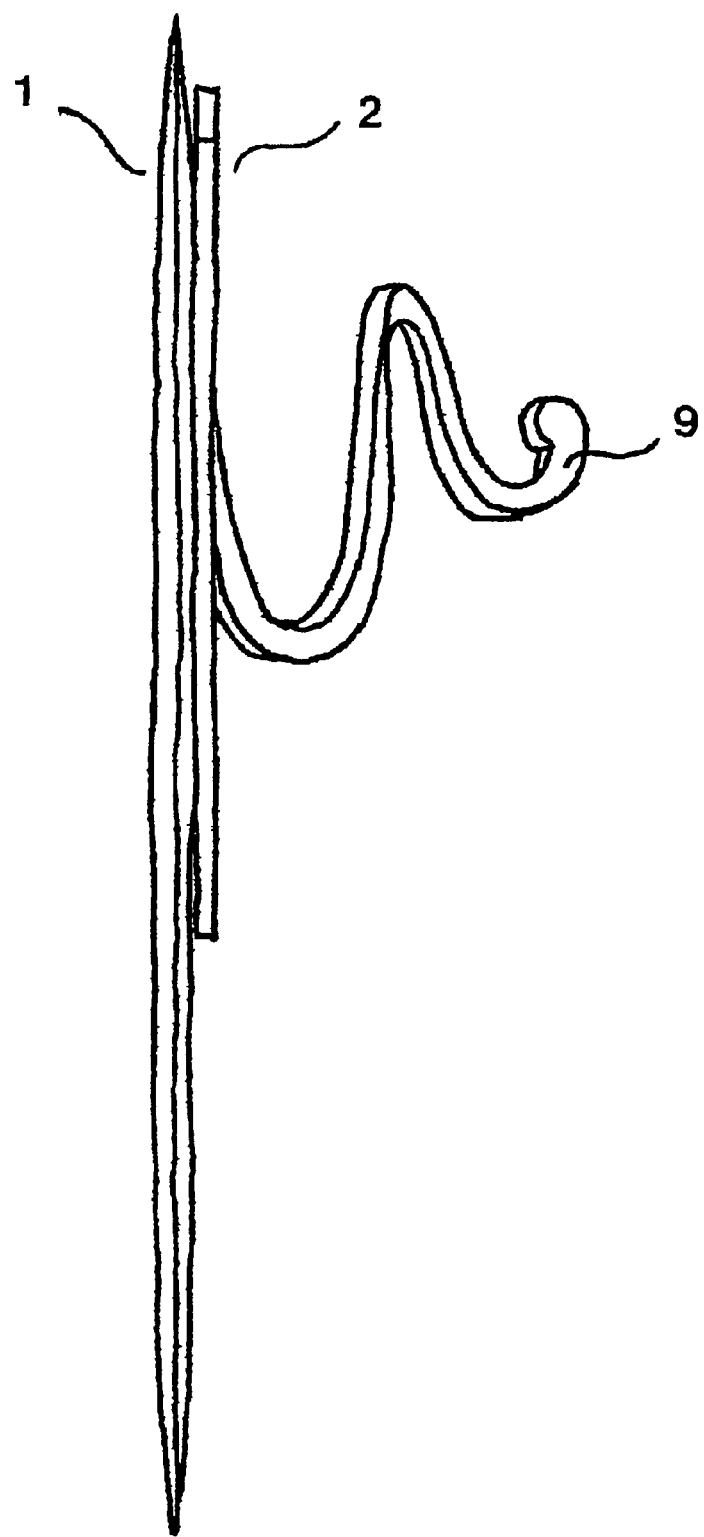
FIG. 4 shows the embodiment shown in FIG. 1 with a part of the helix detached from the flange.

FIG. 3 shows the same embodiment, seen from the side. In FIG. 4, the bag is being prepared for application and a part 9 of a strip defined by a helical weakening line has been removed from the plane of the flange and is ready for tearing off leaving a bag having an aperture better adapted to the stoma than conventional standardised bags.

Figure 5:
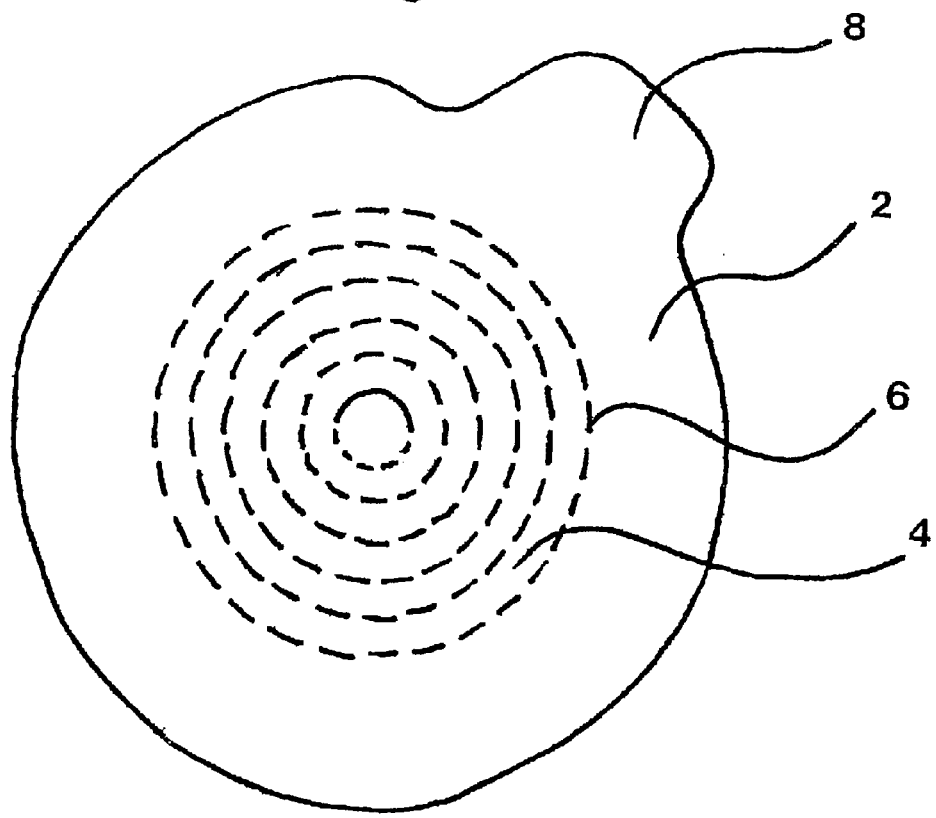
FIG. 5 shows another embodiment of a flange for a collecting bag according to the invention having a predetermined weakening line in the form of concentric lines.

FIG. 5 shows an embodiment of a flange according to the invention having a weakening line pattern 6 in the form of a number of interrupted concentric lines surrounding the aperture 3 in the flange.

Figure 6:
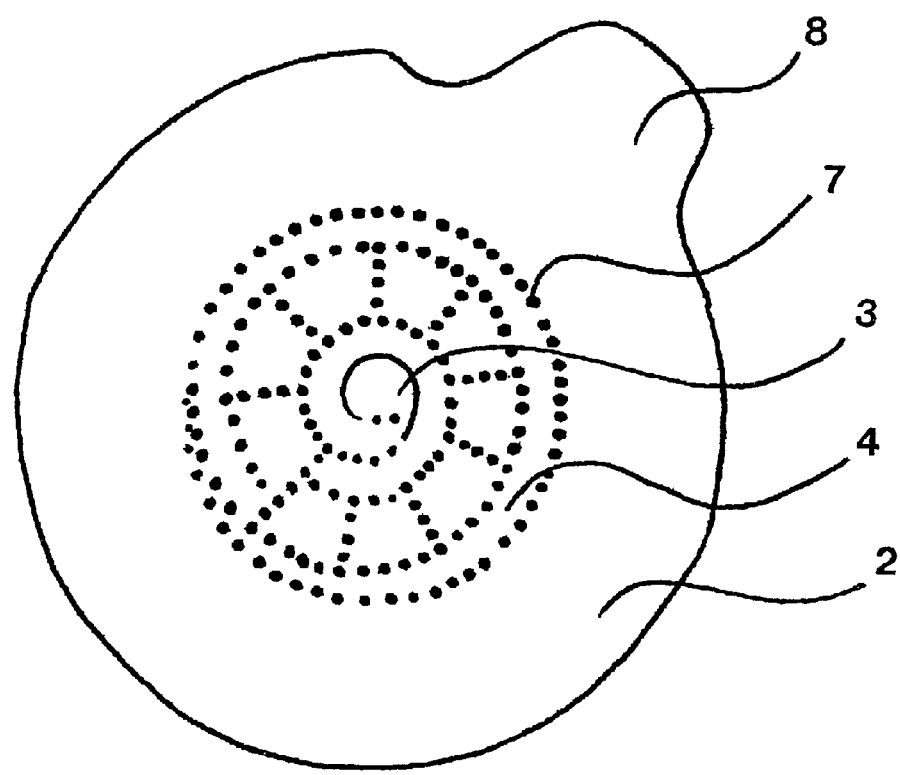
FIG. 6 shows a further embodiment of a flange for a collecting bag according to the invention having a predetermined weakening line in the form of a combination of helical and radial lines.

FIG. 6 shows a further embodiment of a flange according to the invention having a weakening line pattern 7 in the form of a combination of helical or concentric lines and radial lines surrounding the aperture 3 in the flange.

Figure 7:
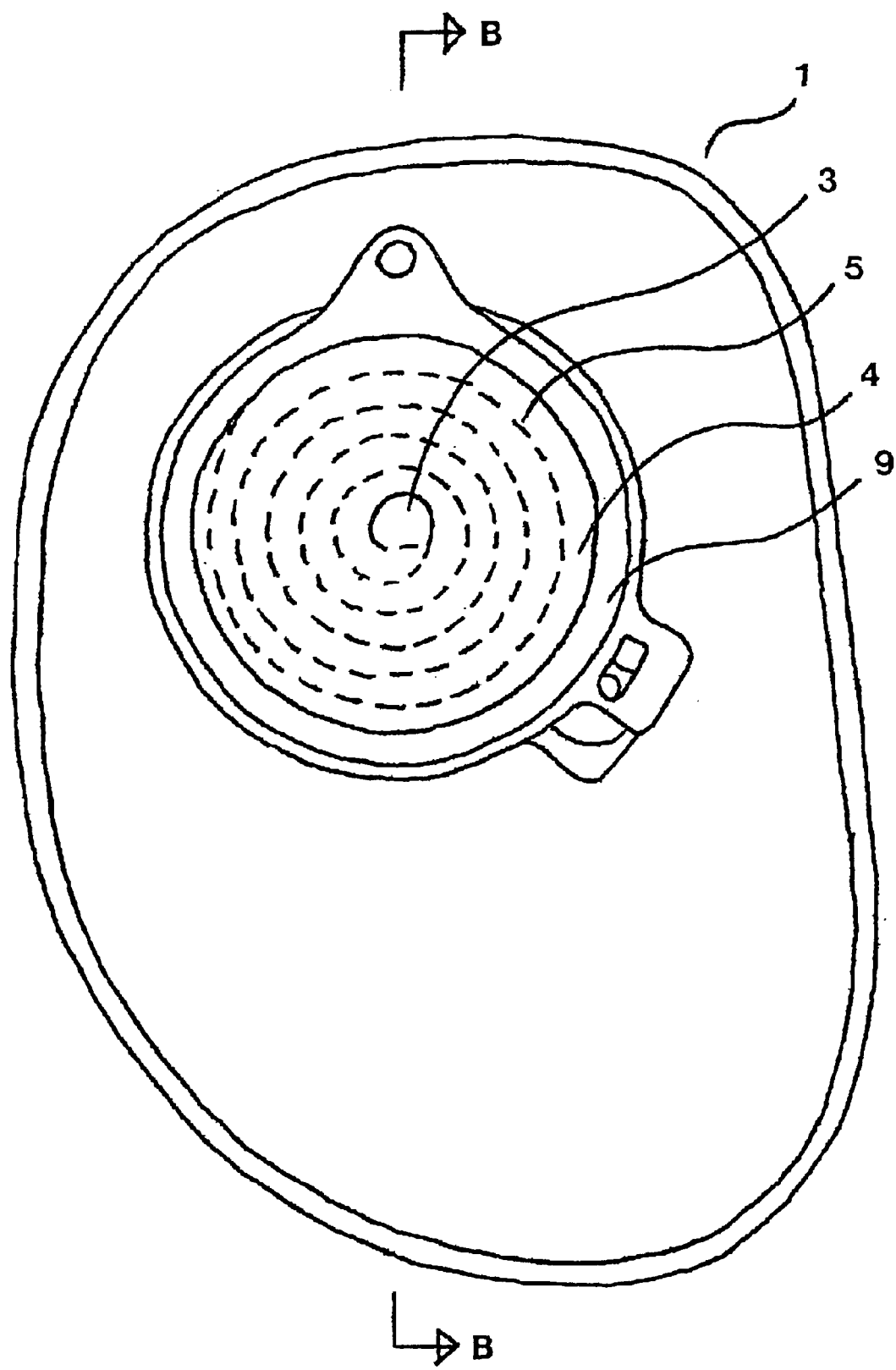
FIG. 7 shows a further embodiment of a collection bag according to the invention having a flange having a predetermined weakening line in the form of a helix and a coupling means.

FIG. 7 shows another embodiment of an ostomy appliance according to the invention. In this embodiment the bag 1 comprises a flange 2 secured to the collecting bag which flange has an inner rim delimiting an inlet aperture 3 therein for receiving a stoma, and wherein the flange has a central area 4 having a predetermined weakening line pattern 5 in the form of a helical line starting from the inner rim thereof. In this embodiment, the flange is surrounded by coupling means 9 in the form of a coupling ring for connecting the bag 1 sealingly with a body side member.

Figure 8:
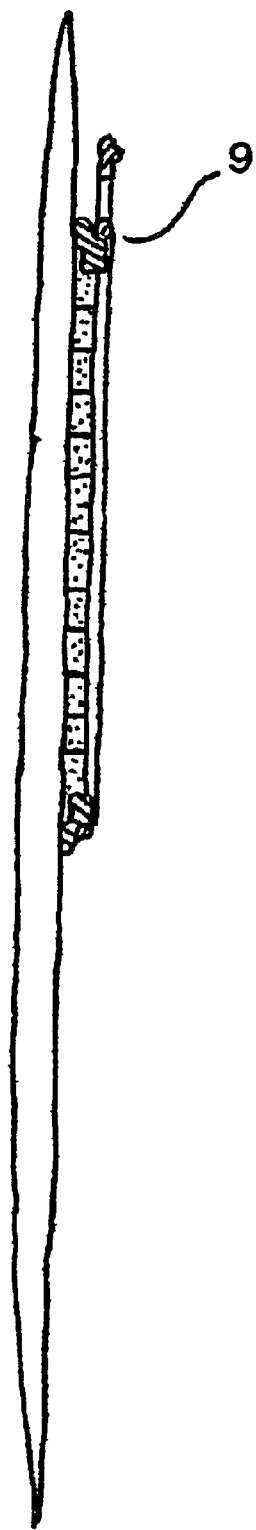
FIG. 8 shows a section of the embodiment shown in FIG. 7 along the line B—B.

FIG. 8 shows a sectional view of the embodiment of FIG. 7 along the line B—B showing the coupling ring 9 secured to the bag outside the central area.

Figure 9:
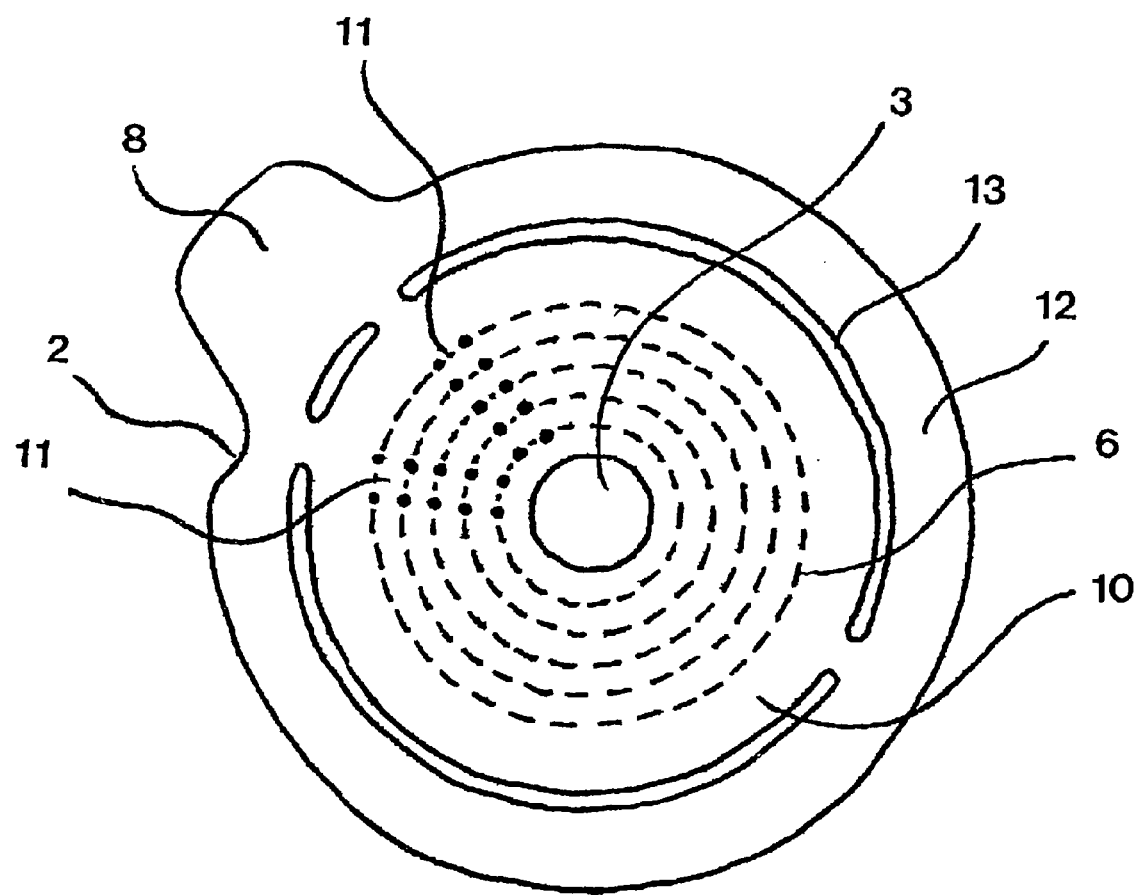
FIG. 9 shows a still further embodiment of a flange for a collecting bag according to the invention having a predetermined weakening line in the form of concentric lines.

FIG. 9 shows a preferred embodiment of a flange according to the invention. The central area of the flange 2 has a weakening line pattern 6 in the form of a number of interrupted concentric lines surrounding the aperture 3 and is surrounded by a substantially annular part 10 of the flange acting as coupling means for connecting a bag sealingly to a body side member. The weakening pattern has at least one interruption 11 in a radial zone from the aperture for receiving the stoma towards the outer periphery and an ear 8 for facilitating the removal of the bag. Such relative enforcement may be in the form of an interruption of the pattern of the weakening line, shown as two sets of "enforcing lines" or interruptions 11 in the line pattern 6. Outside the annular part 10 is preferably an outer part 12 being delimited from the annular part 10 by perforations 13 of the kind disclosed in WO 00/30576 in an essentially circular zone for further reducing the risk of leakage.

The invention being thus described, it will be apparent that the same may be varied in many ways. Such variations are not to be regarded as a departure from the spirit and scope of the invention, and all such modifications as would be recognized by one skilled in the art intended to be included within the scope of the following claims.

What is claimed is:

1. A flange for a medical collecting bag comprising an inner rim delimiting an aperture allowing bodily fluids or exudates to enter the bag, said flange having a central area encircling the aperture which area has a predetermined pattern of weakening lines such that the force needed for removing the bag flange from the skin or a body side member is smaller than the force needed for breaking the weakening lines, said weakening pattern being in the form of punched or cut dots, slots or interrupted rectilinear or curved lines.

2. The flange as claimed in claim 1, wherein the weakening pattern is in the form of an interrupted helical line starting from the inner rim of the flange.

3. The flange as claimed in claim 1, wherein the weakening pattern is in the form of a number of interrupted essentially concentric lines surrounding the aperture.

4. The flange as claimed in claim 1 wherein the weakening pattern is in the form of a combination of helical or concentric lines and radial lines enabling removal of parts of said flange.

5. The flange as claimed in claim 1 wherein the weakening pattern is in the form of concentric lines forming rings and wherein the weakening pattern has at least one interruption in a radial zone from the aperture for receiving the stoma, said interruption having a tear resistance higher than a force necessary to break bridge area connecting the consecutive rings of said flange.

6. A medical appliance comprising a body side member having a flange in the form of an adhesive wafer for securing the appliance to a patient's skin, said wafer having an aperture allowing bodily fluids or exudates to enter the appliance, and a separately exchangeable collecting bag secured to the body side member for collecting fluids or excretions, said flange having an inner rim defining the aperture therein and a central area encircling the aperture which area has a predetermined pattern of weakening lines such that the force needed for removing the bag flange from skin is smaller than the force needed for breaking the weakening lines, said weakening pattern being in the form of punched or cut dots, slots or interrupted rectilinear or curved lines.

7. A medical collecting bag comprising a bag flange having an aperture allowing bodily fluids or exudates to enter the bag, the bag including a coupling element for releasable coupling and sealing to a second corresponding coupling element fixedly connected to a body side member which has an adhesive wafer for securing the body side member to a patient's skin, said wafer having an aperture allowing bodily fluids or exudates to enter the bag, said bag flange having an inner rim defining the aperture therein and a central area encircling the aperture and having a predetermined pattern of weakening lines, the force needed for removing the bag flange from the body side member being smaller than the force needed for breaking the weakening lines, and said weakening pattern being in the form of punched or cut dots, slots or interrupted rectilinear or curved lines.

8. The collecting bag as claimed in claim 6 wherein the central area having a predetermined weakening line pattern does not show adhesive properties.

9. A medical appliance comprising a body side member having an adhesive wafer for securing the appliance to a patient's skin, said wafer having an aperture allowing bodily fluids or exudates to enter the appliance, and a separately exchangeable collecting bag having a bag flange with an aperture allowing bodily fluids or exudates to enter the appliance, said body side member including a first coupling element being fixedly connected to the body side member and the collecting bag including a corresponding second coupling element adapted for releasable coupling and sealing to the body side member, said bag flange having an inner rim defining the aperture therein and a central area with a predetermined pattern of weakening lines, the force needed for removing the bag flange from the body side member being smaller than the force needed for breaking the weakening lines, and the weakening pattern being in the form of punched or cut dots, slots or interrupted rectilinear or curved lines.

10. The appliance according to claim 6 wherein the appliance is an ostomy appliance or bag.

11. The bag as claimed in claim 7 wherein the bag is an ostomy appliance or bag.

12. The flange as claimed in claim 5, wherein said flange includes a protruding part and said interruption is radially directed toward said protruding part.

13. The medical appliance as claimed in claim 9, wherein the weakening pattern is in the form of an interrupted helical line starting from the inner rim of the bag flange.

14. The medical appliance as claimed in claim 9, wherein the weakening pattern is in the form of a member of interrupted essentially concentric lines surrounding the aperture of the bag flange.

15. The medical appliance as claimed in claim 9 wherein the weakening pattern is in the form of a combination of helical or concentric lines and radial lines enabling removal of parts of said bag flange.

16. The medical appliance as claimed in claim 9 wherein the weakening pattern is in the form of concentric lines forming rings and wherein the weakening pattern has at least one interruption in a radial zone from the aperture, said interruption having a tear resistance higher than a force necessary to break bridge areas connecting the consecutive rings of said bag flange.

17. The medical appliance as claimed in claim 16, wherein said bag flange includes a protruding part and said interruption is radially directed toward said protruding part.

* * * * *